United States Patent [19]

Mills

[11] Patent Number: 5,519,460
[45] Date of Patent: May 21, 1996

[54] VISOR SUNGLASSES

[76] Inventor: Christopher T. Mills, Rural Route 3, Box 7024, Jonestown, Pa. 17038

[21] Appl. No.: 402,535

[22] Filed: Mar. 10, 1995

[51] Int. Cl.⁶ .............................. G02C 7/10; A61F 9/00
[52] U.S. Cl. ..................... 351/44; 351/47; 2/13
[58] Field of Search ................... 351/44, 47, 57, 351/58, 59, 153, 155, 158, 86, 41; 2/12, 13, 10

[56] References Cited

U.S. PATENT DOCUMENTS

| | | | |
|---|---|---|---|
| 3,238,005 | 3/1966 | Petitto | 2/13 |
| 5,335,025 | 8/1994 | Wang | 2/13 |

*Primary Examiner*—William L. Sikes
*Assistant Examiner*—Hung Xuan Dang

[57] ABSTRACT

A pair of sunglasses for shielding glare and filtering light directed into human eyes. The inventive device includes a frame having ear pieces pivotally mounted thereto. A lens is removably mounted to the frame for filtering light passing through the lens. A visor is mounted to the frame so as to project outwardly therefrom to reduce glare into the eyes of the wearer.

4 Claims, 3 Drawing Sheets

VISOR SUNGLASSES

BACKGROUND OF THE INVENTION

1. Field of the Invention

The present invention relates to eye protection devices and more particularly pertains to a pair of visor sunglasses for shielding glare and filtering light directed into human eyes.

2. Description of the Prior Art

The use of eye protection devices is known in the prior art. More specifically, eye protection devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art eye protection devices include U.S. Pat. No. 5,208,916; U.S. Pat. No. 4,976,530; U.S. Pat. No. 4,955,087; U.S. Pat. No. 4,869,586; U.S. Pat. No. Des. 317,771; and U.S. Pat. No. Des. 300,329.

While these devices fulfill their respective, particular objectives and requirements, the aforementioned patents do not disclose a pair of visor sunglasses for shielding glare and filtering light directed into human eyes which includes a frame having ear pieces pivotally mounted thereto, a lens removably mounted to the frame for filtering light passing through the lens, and a visor mounted to the frame so as to project outwardly therefrom to reduce glare into the eyes of the wearer.

In these respects, the visor sunglasses according to the present invention substantially departs from the conventional concepts and designs of the prior art, and in so doing provides an apparatus primarily developed for the purpose of shielding glare and filtering light directed into human eyes.

SUMMARY OF THE INVENTION

In view of the foregoing disadvantages inherent in the known types of eye protection devices now present in the prior art, the present invention provides a new pair of visor sunglasses construction wherein the same can be utilized for protecting eyes of a wearer from both glare and bright light. As such, the general purpose of the present invention, which will be described subsequently in greater detail, is to provide a new pair of visor sunglasses apparatus and method which has many of the advantages of the eye protection devices mentioned heretofore and many novel features that result in a pair of visor sunglasses which is not anticipated, rendered obvious, suggested, or even implied by any of the prior art eye protection devices, either alone or in any combination thereof.

To attain this, the present invention generally comprises a pair of sunglasses for shielding glare and filtering light directed into human eyes. The inventive device includes a frame having ear pieces pivotally mounted thereto. A lens is removably mounted to the frame for filtering light passing through the lens. A visor is mounted to the frame so as to project outwardly therefrom to reduce glare into the eyes of the wearer.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new pair of visor sunglasses apparatus and method which has many of the advantages of the eye protection devices mentioned heretofore and many novel features that result in a pair of visor sunglasses which is not anticipated, rendered obvious, suggested, or even implied by any of the prior art eye protection devices, either alone or in any combination thereof.

It is another object of the present invention to provide a new pair of visor sunglasses which may be easily and efficiently manufactured and marketed.

It is a further object of the present invention to provide a new pair of visor sunglasses which is of a durable and reliable construction.

An even further object of the present invention is to provide a new pair of visor sunglasses which is susceptible of a low cost of manufacture with regard to both materials and labor, and which accordingly is then susceptible of low prices of sale to the consuming public, thereby making such visor sunglasses s economically available to the buying public.

Still yet another object of the present invention is to provide a new pair of visor sunglasses which provides in the apparatuses and methods of the prior art some of the advantages thereof, while simultaneously overcoming some of the disadvantages normally associated therewith.

Still another object of the present invention is to provide a new pair of visor sunglasses for shielding glare and filtering light directed into human eyes.

Yet another object of the present invention is to provide a new pair of visor sunglasses which includes a frame having ear pieces pivotally mounted thereto, a lens removably mounted to the frame for filtering light passing through the lens, and a visor mounted to the frame so as to project outwardly therefrom to reduce glare into the eyes of the wearer.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
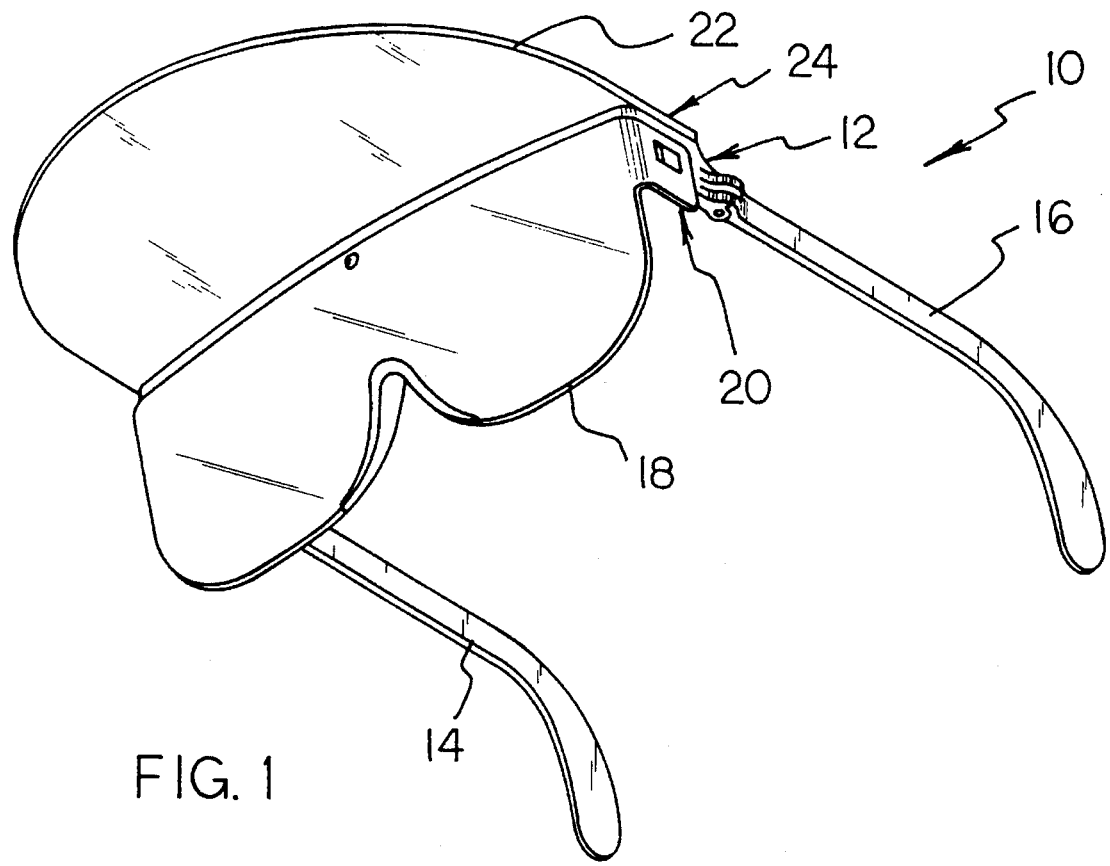
FIG. 1 is an isometric illustration of a pair of visor sunglasses according to the present invention.

With reference now to the drawings, and in particular to FIGS. 1–6 thereof, a new pair of visor sunglasses embodying the principles and concepts of the present invention and generally designated by the reference numeral 10 will be described.

More specifically, it will be noted that the visor sunglasses 10 according to the present invention comprise a frame 12 having a first ear piece 14 pivotally mounted thereto and a second ear piece 16 pivotally mounted such that the frame 12 can be engaged to respectively opposed ears of an individual wearing the device 10. A lens 18 is removably mounted to the frame 12 by a lens coupling means 20. The lens 18 engages a nose of the wearer so as to support the frame 12 above the eyes of a wearer. A visor 22 is mounted to the frame 12 by a visor coupling means 24 and projects outwardly from the frame 12 so as to reduce glare into the eyes of the wearer.

Figure 2:
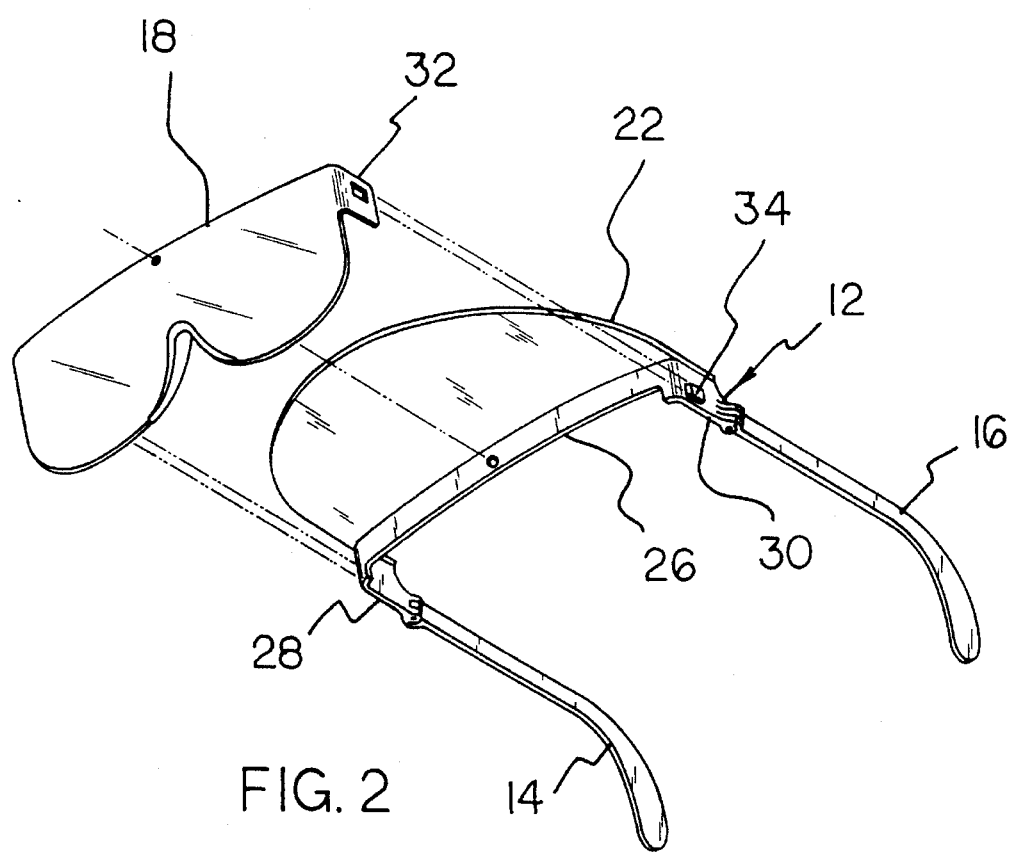
FIG. 2 is an exploded isometric illustration of the invention.
Figure 3:
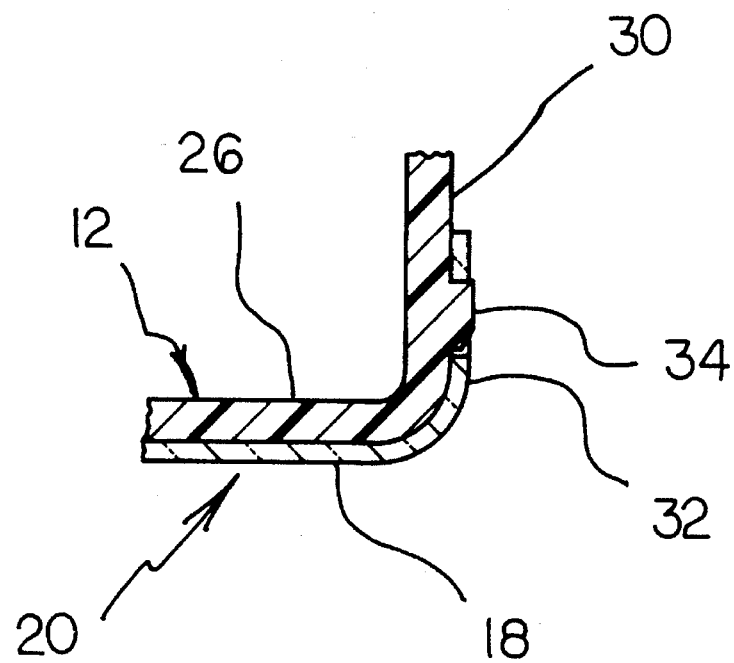
FIG. 3 is an enlarged cross-sectional view of a lens coupling means of the present invention.
Figure 4:
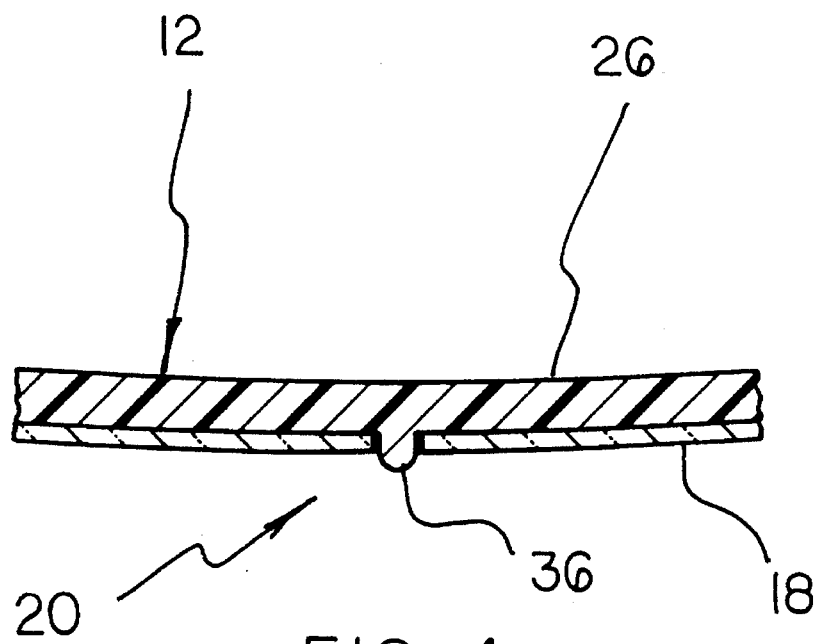
FIG. 4 is an enlarged cross-sectional view of the lens coupling means.

As best illustrated in FIGS. 2 through 4, the frame 12 according to the present invention 10 comprises an elongated center portion 26 having a first lateral portion 28 projecting from a first end thereof, and a second lateral portion 30 projecting from a second end thereof. The first ear piece 14 is pivotally mounted to a distal end of the first lateral portion 28, with the second ear piece 16 being similarly pivotally mounted to the distal end of the second lateral portion 30. By this structure, the first ear piece 14 and the second ear piece 16 can be flatly folded into a substantially parallel orientation relative to the center portion 26 of the frame 12 for storage of the device 10.

With continuing reference to FIGS. 2 through 4, it can be shown that the lens coupling means 20 according to the present invention 10 comprises an unlabelled first lateral tab projecting from a first side of the lens 18 and a second lateral tab 32 projecting from a second side of the lens 18. The lateral tabs are substantially similar in design and configuration, and therefore only the second lateral tab 32 will be described in detail. The lens coupling means 20 further includes securing projections 34 extending from the lateral portions 28 of the frame 12. The securing projections 34, as best illustrated in FIG. 3, are configured so as to extend through unlabelled apertures in the lateral tabs 32. Preferably, the securing projection 34 and the aperture through the lateral tab are cooperatively configured so as to define a substantially rectangular shape which precludes pivoting of the lens 18 relative to the frame 12. By this structure, the lens 18 can be simply snapped into securement with the frame 12 as shown in FIG. 1.

Referring now to FIG. 4, it can be shown that the lens coupling means 20 according to the present invention 10 further comprises an alignment projection 36 extending from the center portion 26 of the frame 12 which is received through an unlabelled aperture extending through the lens 18 so as to align the lens 18 relative to the frame 12. By this structure, the lens coupling means 20 ensures proper alignment of the lens 18 relative to the frame 12 during coupling of the lens 18 thereto.

Figure 5:
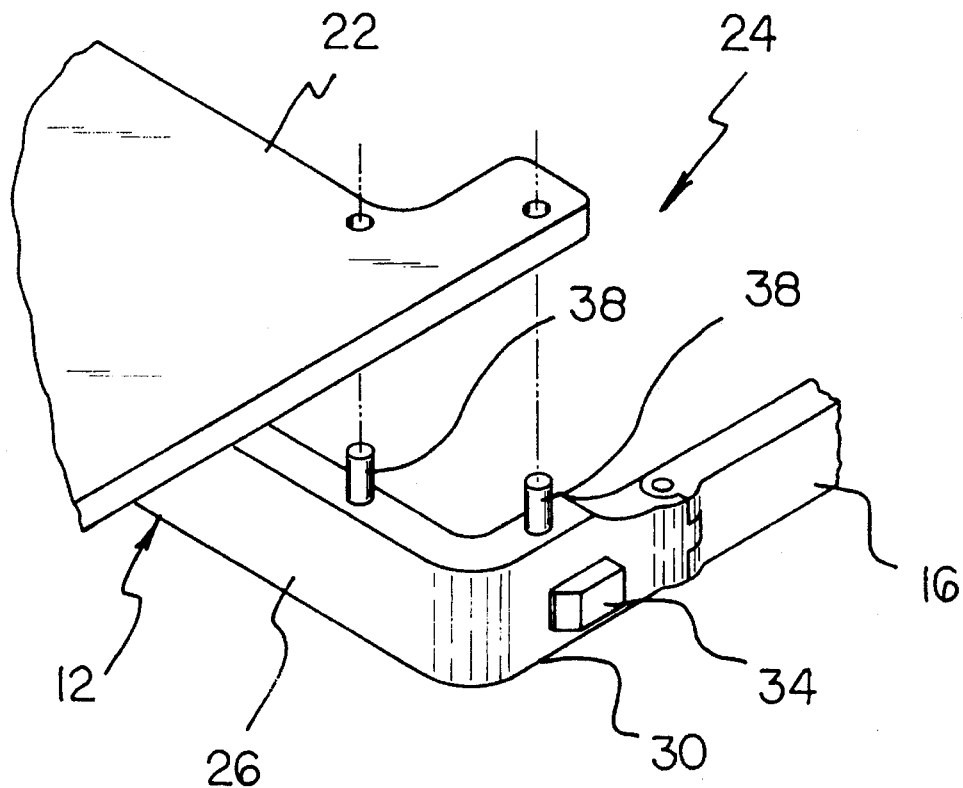
FIG. 5 is an exploded and enlarged isometric illustration of a visor coupling means according to the present invention.
Figure 6:
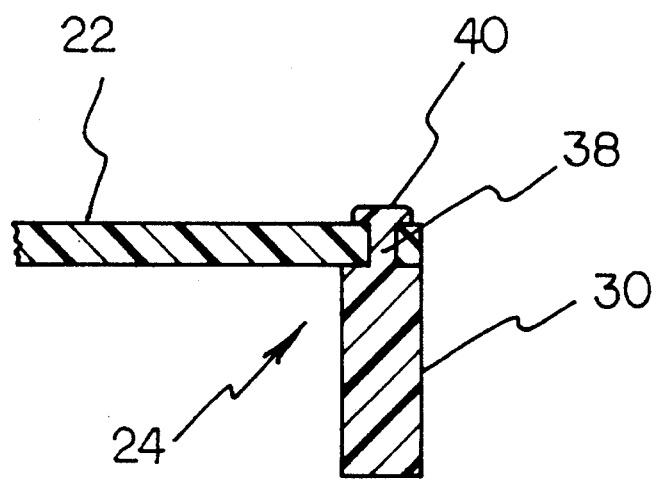
FIG. 6 is a cross-sectional view of a portion of the visor coupling means.

Referring now to FIGS. 5 and 6, it can be shown that the visor coupling means 24 of the present invention 10 comprises a plurality of mounting pegs 38 extending from the frame 12 and projecting through unlabelled apertures in the visor 22. Preferably, a plurality of the mounting pegs 38 project from the center portion 26 of the frame 12, with a further plurality of mounting pegs 38 projecting from the lateral portions 28 and 30 thereof. The mounting pegs 38 can simply be frictionally engaged to interior surfaces of the apertures within the visor 22 through which they project so as to removably couple the visor 22 relative to the frame 12. However, and as shown in FIG. 6, the mounting pegs 38 can be shaped so as to define a flattened head 40 facilitating permanent securement of the visor 22 to the frame 12 if so desired. In this connection, the frame 12 is desirably molded from a thermoplastic material, wherein the mounting pegs 38 are integrally formed therewith such that the mounting pegs once positioned through the apertures and the visor 22, can be heated and deformed so as to define the flattened head 40 securing the visor 22 permanently to the frame 12.

In use, the visor sunglasses 10 according to the present invention can be easily utilized to shield glare from above a user's eyes and further to filter light passing through the lens 18 prior to admittance of such light into the eyes of the wearer. The removable coupling between the lens 18 and the frame 12, and between the visor 22 and the frame 12 if so desired, limits the device 10 to be selectively constructed and deconstructed for storage and/or travelling purposes. Further, it is within the intent and purview of the present invention to provide a plurality of disparate lenses 18 which can be interchangeably coupled to the frame 12, as well as a plurality of disparate visors 22 which can also be interchangeably coupled to the frame 12 as desired.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A pair of visor sunglasses comprising:

a frame having first and second ear pieces pivotally mounted thereto, said frame having an elongated center portion with a first lateral portion projecting from a first end thereof, and a second lateral portion projecting from a second end thereof, the first ear piece being pivotally mounted to a distal end of the first lateral portion, and the second ear piece being pivotally mounted to the distal end of the second lateral portion;

a lens mounted to the frame;

a visor mounted to the frame and projecting outwardly from the frame so as to reduce glare into the eyes of the wearer; a visor coupling means for removably coupling the lens to the frame;

a lens coupling means for removeably coupling the lens to the frame having a first lateral tab projecting from a first side of the lens, and a second lateral tab projecting from a second side of the lens; securing projections extending from the lateral portions of the frame, the securing projections extending through apertures in the lateral tabs, said securing projections and the apertures through the lateral tabs are cooperatively configured so as to define a substantially rectangular shape which precludes pivoting of the lens relative to the frame.

2. The visor sunglasses of claim 1 wherein the lens coupling means further comprises an alignment projection extending from the center portion of the frame which is received through an aperture extending through the lens so as to align the lens relative to the frame.

3. The visor sunglasses of claim 2, wherein the visor coupling means comprises a plurality of mounting pegs extending from the frame and projecting through apertures in the visor.

4. The visor sunglasses of claim 3, wherein a plurality of the mounting pegs project from the center portion of the frame, with a further plurality of mounting pegs projecting from the lateral portions of the frame, the mounting pegs projecting through and frictionally engaging interior surfaces of apertures within the visor to removably couple the visor relative to the frame.

* * * * *